(12) United States Patent
Wei et al.

(10) Patent No.: US 6,239,251 B1
(45) Date of Patent: May 29, 2001

(54) END-FUNCTIONALIZED ANILINE-BASED OLIGOMERS, CORROSION-RESISTANT COPOLYMERS AND METHODS OF MAKING THE SAME

(75) Inventors: Yen Wei; Chuncai Yang; Tianzhong Ding; Xinru Jia; Danliang Jin; Jui-Ming Yeh; Jianguo Wang, all of Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 09/062,005

(22) Filed: Apr. 17, 1998

Related U.S. Application Data

(63) Continuation of application No. PCT/US96/16773, filed on Oct. 18, 1996.
(60) Provisional application No. 60/013,992, filed on Mar. 20, 1996, and provisional application No. 60/005,731, filed on Oct. 20, 1995.

(51) Int. Cl.[7] .............................. C08G 73/00; C25B 3/02
(52) U.S. Cl. ..................... 528/422; 528/230; 528/243; 528/492; 204/78; 204/72; 204/59 R
(58) Field of Search ..................................... 528/422, 230, 528/243; 204/78, 72, 59 R

(56) References Cited

U.S. PATENT DOCUMENTS

| | | |
|---|---|---|
| 3,975,243 | 8/1976 | Levinos . |
| 4,586,792 | 5/1986 | Yang et al. . |
| 4,615,829 | 10/1986 | Tamura et al. . |
| 4,629,540 | 12/1986 | Geniees et al. . |
| 4,698,391 | 10/1987 | Yacobucci et al. . |
| 4,699,804 | 10/1987 | Miyata et al. . |
| 4,769,115 | 9/1988 | Satoh et al. . |
| 4,940,514 | * 7/1990 | Wei ........................................ 204/78 |
| 4,940,517 | 7/1990 | Wei . |
| 4,986,886 | 1/1991 | Wei et al. . |
| 5,120,807 | 6/1992 | Wei et al. . |

OTHER PUBLICATIONS

Andreatta, et al., "Electrically–Conductive Fibers of Polyaniline Spun from Solutions in Concentrated Sulfuric Acid", Synthetic Metals, vol. 26, pp. 383–389 (1988).

(List continued on next page.)

*Primary Examiner*—Duc Truong
(74) *Attorney, Agent, or Firm*—Akin, Gump, Strauss, Hauer & Feld, L.L.P.

(57) ABSTRACT

Methods of forming low molecular weight oligomers of aniline-based compounds are provided as well as methods of forming varied molecular weight oligomers and polymers that are aniline-based which are end-functionalized and capable of being reacted with other monomeric species to form a variety of copolymers. The oligomers, end-functionalized oligomers and copolymers exhibit corrosion-resistant properties and provide corrosion-resistant compounds for use on various substrates.

15 Claims, 2 Drawing Sheets

OTHER PUBLICATIONS

Antoon, et al., "Crosslinking Mechanism of an Anhydride–Cured Expoxy Resin as Studied by Fourier Transform Infrared Spectroscopy", J. Poly Sci.: Poly. Chem. Ed., vol. 19, pp. 549–570 (1981).

Bidan, et al., "Poly(2–propylaniline): an electroactive polymer, soluble in organic medium in the reduced state", J. Electroanal. Chem., vol. 271, pp. 59–68 (1989).

Cao, et al., "Influence of Chemical Polymerization Conditions of the Properties of Polyaniline", Polymer, vol. 30, pp. 2305–2311 (Dec. 1989).

Cao, et al., "Counter–Ion Induced Processibility of Conducting Polyaniline", Synthetic Metals, vol. 55–57, pp. 3514–3519 (1993).

Guay, et al., "Synthesis and Characterization of Poly(diarylamines). A New Class of Electrochromic Conducting Polymers", Macromolecules, vol. 23, pp. 3598–3605 (1990).

Hádek, et al., "Electric Properties of Donor–Acceptor Complexes of Oligoanilinic Compounds", Coll. Czech. Chem. Commun., vol. 34, pp. 3139–3145 (1969).

Harada, et al., "Vibrational Spectra and Structure of Polyaniline and Related Compounds", Synthetic Metals, vol. 29, pp. E303–E312 (1989).

Honzl, et al., "Organic Semiconductors: Donor–Acceptor Complexes of Conjugated Bases with a Repeating Structural Unit", Chem. Commun., No. 19, pp. 440–441 (1965).

Honzl, et al., "Polyaniline Compounds. The Linear Oligoaniline Derivatives Tri–, Tetra–, and Hexaanilinobenzene and Their Conductive Complexes", J. Polymer Sci.: Part C, No. 22, pp. 451–462 (1968).

Jain, et al., "Formation of an Active Electronic Barrier at Al/Semiconductor Interfaces: A Novel Approach in Corrosion Prevention", Corrosion–NACE, vol. 42, No. 12, pp. 700–707 (Dec. 1986).

Kharasch, et al., "The Condensation of Butyraldehyde and Aniline", J. Amer. Chem. Soc., vol. 62, pp. 494–497 (1940).

Kitani, et al., "A Conducting Polymer Derived from Para–Aminodiphenylamine", J. Electroanal. Chem., vol. 221, pp. 69–82 (1987).

Enns, et al., "Torsional Braid Analysis", pp. 27–63 (1983).

Ladenberg, A., "Ueber die Aldehydine, eine neue Klasse Basen", Chem. Ber., vol. 11, pp. 590–600 (1878).

Leclerc, et al., Synthesis and Characterization of Poly(alkylanilines), Macromolecules, vol. 22, pp. 649–653 (1989).

Wudl, et al., "Phenyl–Capped Octaaniline (COA): An Excellent Model for Polyaniline", J. Amer. Chem. Soc., vol. 108, pp. 8311–8313 (1986).

Lu, et al., "Corrosion Protection of Mild Steel by Coatings Containing Polyaniline", Synthetic Metals, vol. 71, pp. 2163–2166 (1995).

MacDiarmid, et al., "Polyaniline: Interconversion of Metallic and Insulating Forms", Mol. Cryst. Liq. Cryst., vol. 121, pp. 173–180 (1985).

MacDiarmid, et al., "Polyaniline: Protonic Acid Doping to the Metallic Regime", Mol. Cryst. Liq. Cryst., vol. 125, pp. 309–318 (1985).

MacDiarmid, et al., "Polyaniline: Electrochemistry and Application to Rechargeable Batteries", Synthetic Metals, vol. 18, pp. 393–398 (1987).

MacInnes, Jr., et al., "Poly–o–Methoxyaniline: A New Soluble Conducting Polymer", Synthetic Metals, vol. 25, pp. 235–242 (1988).

Mijovic, et al., "Reaction Kinetics of Epoxy/Amine Model Systems", Macromolecules, vol. 27, pp. 7589–7600 (1994).

Min, et al., "Concept of 'Secondary Doping' As Applied to Polyaniline", J. Polymer Prep., vol. 35, No. 1, pp. 231–232 (1994).

Morgan, et al., "Aromatic Azomethine Polymers and Fibers", Macromolecules, vol. 20, pp. 729–739 (1987).

Nguyên, et al., "Electrochemical, Electrochromic, and Conductive Properties of Poly(N–alkyldiphenylamine) Polymers", J. Chem. Soc., Chem. Commun., pp. 1221–1222 (1990).

Oh, et al., "Polyaniline: Dependency of Selected Properties on Molecular Weight", Synthetic Metals, vol. 55–57, pp. 977–982 (1993).

Salaneck, et al., "Physical Characterization of Some Polyaniline, $(ØN)_x$", Mol. Cryst. Liq. Cryst., vol. 121, pp. 191–194 (1985).

Sariciftci, et al., "Structural and Electronic Transitions in Polyaniline: A Fourier Transform Infrared Spectroscopic Study", J. Chem. Phys., vol. 92, No. 7, pp. 4530–4539 (1990).

Smith, et al., "The Effect of Electronegative Substituents on the Reductive Dimerization of Schiff Bases," J. Org. Chem., vol. 38, No. 16, pp. 2776–2779 (1973).

Tabei, et al., "The Nuclear Magnetic Resonance and Infrared Spectra of Aromatic Azomethines", Bull. of the Chem. Soc. of Japan, vol. 42, pp. 1440–1443 (1969).

Tang, et al. "Molecular Weight of Chemically Polymerized Polyaniline", Makromol. Chem., Rapid Commun., vol. 9, pp. 829–834 (1988).

MacDiarmid, et al., "Electrochemical Characteristics of 'Polyaniline' Cathodes and Anodes in Aqueous Electrolytes", Mol. Cryst. Liq. Cryst., vol. 121, pp. 187–190 (1985).

Tang, et al., "Infrared Spectra of Soluble Polyaniline", Synthetic Metals, vol. 24, pp. 231–238 (1988).

Wei, et al., "Electrochemical Polymerization of Thiophenes in the Presence of Bithiophene or Terthiophene: Kinetics and Mechanism of the Polymerization", Chem. Mater., vol. 3, pp. 888–897 (1991).

Wei, et al., "Preparation and Conductivities of Fullerene-–doped Polyanilines", J. Chem. Soc., Chem. Commun., pp. 603–604 (1993).

Wei, et al., ". . . Electrochemistry of Alkyl Ring–Substituted Polyanilines", J. Phys. Chem., vol. 93, pp. 495–499 (1989).

Wei, et al., "Thermal Analysis of Chemically Synthesized Polyaniline and Effects of Thermal Aging on Conductivity", J. Polymer Sci.: Part A, vol. 27, pp. 4351–4363 (1989).

Wei, et al., "A Study of Leucoemeraldine and the Effect of Redox Reactions on the Molecular Weight of Chemically Prepared Polyaniline", Macromolecules, vol. 27, pp. 518–525 (1994).

Wei, et al., "Thermal Transitions and Mechanical Properties of Films of Chemically Prepared Polyaniline", Polymer, vol. 33, No. 2, pp. 314–322 (1992).

Wei, et al., "Monitoring the Chemical Polymerization of Aniline by Open–Circuit–Potential Measurements", Polymer, vol. 35, No. 16, pp. 3572–3575 (1994).

Wei, et al., "Polyaniline as Corrosion Protection Coatings on Cold Rolled Steel", Polymer, vol. 36, No. 23, pp. 4535–4537 (1995).

Wei, et al., "Electrochemical Studies of Corrosion Inhibiting Effect of Polyaniline Coatings", Poly. Mater. Sci. & Eng., vol. 72, pp. 563–564 (1995).

Wei, et al., "A One–Step Method to Synthesize N, N'–Bis(4'–Aminophenyl)–1,4–Quinonenediimine and Its Derivatives", Tetrahedron Let., vol. 37, No. 6, pp. 731–734 (1996).

Wrobleski, et al., "Corrosion Resistant Coatings from Conducting Polymers", Polymer Prep., vol. 35, No. 1, pp. 265–266 (1994).

Watanabe, et al., "Electrochemical Polymerization of Aniline and N–Alkylanilines", Macromolecules, vol. 22, pp. 3521–3525 (1989).

Wessling, B., "On the Structure of Binary Conductive Polymer/Solvent Systems", Synthetic Metals, vol. 41–43, pp. 907–910 (1991).

Wessling, B., "Electrical Conductivity in Heterogeneous Polymer Systems", Synthetic Metals, vol. 41–43, pp. 1057–1062 (1991).

Wudl, et al., "Poly(p–phenyleneamineimine): Synthesis and Comparison to Polyaniline", J. Am. Chem. Soc., vol. 109, pp. 3677–3684 (1987).

Xia, et al., "Camphorsulfonic Acid Fully Doped Polyaniline Emeraldine Salt . . . ", Macromolecules, vol. 27, pp. 7212–7214 (1994).

Yang, et al., "Conjugated Aromomatic Polyimines", Macromolecules, vol. 28, pp. 1180–1196 (1995).

Clougherty, et al., "C=N Stretching Frequency in Infrared Spectra of Aromatic Azomethines", J. Org. Chem., vol. 22, p. 462 (Oct. 1956).

Shenglong, et al., "Polymerization of Substituted Aniline and Characterization of the Polymers Obtained", Synthetic Metals, vol. 16, pp. 99–104 (1986).

Travers, et al., "Transport and Magnetic Resonance Studies of Polyaniline", Mol. Cryst. Liq. Cryst., vol. 121, pp. 195–199 (1985).

Wang, et al., "The Effect of Anions of Supporting Electrolyte on the Electrochemical polymerization of Aniline and the Properties of Polyaniline", Synthetic Metals, vol. 13, pp. 329–334 (1986).

Watanabe, et al., "Molecular Weight of Electropolymerized Polyaniline", J. Chem. Soc.: Chem. Commun., No. 1, p. 3 (1987).

R. Alkire, et al., "The Critial Geometry for Initiation of Crevice Corrosion", J. Electrochem. Soc., vol. 132, No. 5., pp. 1027–1031, (1985).

Z. Deng, et al., "Stabilization of Metal–Metal Oxide Surfaces Using Electroactive Polymer Films", J. Electrochem. Soc., vol. 136, No. 8, pp. 2152–2158, (1989).

S. Jasty, et al., "Corrosion Prevention Capability of Polyaniline (Emeraldine Base and Salt): An XPS Study", Polym. Mater. Sci. Eng., Vo. 72, pp. 565–566 (1995).

F.–L. Lu, et al., "Phenyl–Capped Octaaniline (COA): An Excellent Model for Polyaniline", J. Am. Chem. Soc., vol. 108, No. 26, pp. 8311–8313, (1986).

V.S. Misra, et al., "Possible Antituberculous Compounds. Part IX. Preparation of Benzlidene and Benzyl Derivatives of 4–Aminodiphenylamine", Jour. Indian Chem. Soc., Vo. 37, No. 8, pp. 481–482 (1960).

A. Tachibana, et al., ". . . Control of Organic Superconductivity", Synthetic Metals, vol. 19, pp. 99–104, (1987).

Y. Wei, et al., "A New Method for Polymerizaation of Pyrrole and Derivatives", Makromol. Chem., Rapid Commun., vol. 12, pp. 617–623 (1991).

Y. Wei, et al., "Spectroscopic and Molecular Weight Studies of Polytoluidines", Mat. Res. Soc. Symp. Proc., vol. 173, pp. 341–346, (1990).

E.M. Genies, et al., "Electrochemical Study of Polyaniline in Aqueous and Organic Medium, Redox and Kinetic Properties", Mol. Cryst. Liq. Cryst., vol. 121, pp. 181–186 (1985).

Diana J. Gerbi, et al., "Thermotropic Polyurethanes", Polymer Preprints, vol. 33, No. 1, pp. 1109–1110 (1992).

Robert W. Layer, "The Chemistry of Imines", pp. 489–510 (1962).

My T. Nguyèn, et al., "Electrochemical, Electrochromic, and Conductive Properties of Poly(N–alkyldiphenylamine) Polymers", J. Chem. Soc., Chem. Comm., pp. 1221–1222 (1990).

S. Sathyanarayanan, et al., "Soluble Conducting Poly Ethoxy Aniline As an Inhibitor for Iron in HCI", Corrosion Science, vol. 33, pp. 1831–1841 (1992).

Wang Shenglong, et al., "Polymerization of Substituted Aniline and Characterization of the Polymers Obtained", Synthetic Metals, vol. 16, pp. 99–104 (1986).

Wei, et al., "Redox Chemistry of Polyaniline", Macromolecules, vol. 27, No. 2, pp. 519–525 (1994).

Bernhard Wessling, "Passivation of Metals by Coating with Polyaniline: Corrosion Potential Shift and Morphological Changes", Adv. Mater, vol. 6., No. 3, pp. 226–228 (1994).

Chen–Jen Yang, et al., "Conjugated Aromatic Polyimines. 2. Synthesis, Structure, and Properties of New Aromatic Polyazomethines", Macromolecules, vol. 28, No. 4, pp. 1180–1196 (1995).

Neil J. Coville, et al., "Oxidative Cyclodehydrogenation of Aromatic Bis(o–aminoanils)", J. Org. Chem., vol. 42, No. 22, pp. 3485–3491 (1977).

Giuseppe D'Aprano, et al., "Synthesis and Characterization of Polyaniline Derivatives: Poly(2–alkoxyanilines) and Poly (2,5–dialkoxyanilines)", Chem. Mater., vol. 7, No. 1, pp. 33–42 (1995).

A.F. Diaz et al., "Electroactive Polyaniline Films", J. Electroanal. Chem., vol. 111, pp. 111–114 (1980).

R.S. Duran, et al., "Polymerization of Conducting Polymers Confined to Free Surfaces: A Comparison of the Langmuir–Blodgett Polymerizations of 3–Alkyl Pyrroles and 2–Alkyl Anilines", Polymer, vol. 33, No. 19, pp. 4019–4023 (1992).

A.J. Epstein, et al., "Insulator–to–Metal Transition in Polyaniline", Synthetic Metals, vol. 18, pp. 303–309 (1987).

D.P. Fasce, et al., "Curing of Epoxy Resins with In Situ––Generated Substituted Ureas", J. Appl. Poly. Sci., vol. 39, pp. 383–394 (1990).

Walter W. Focke, et al., "Influence of Oxidation State, pH, and Counterion on the Conductivity of Polyaniline", J. Phys. Chem., vol. 91, pp. 5813–5818 (1987).

J.H. Fu, et al., "Mid– and Near–Infrared Spectroscopic Investigations of Reactions Between Phenyl Gycidyl Ether (PGE) and Aromatic Amines", J. Appl. Poly. Sci., vol. 49, pp. 219–227 (1993).

E.M Geniès, et al., "Polyaniline: A Historical Survey", Synthetic Metals, vol. 36, pp. 139–182 (1990).

Y. Wei et al., "Polymerization of Aniline and Alkyl Ring–Substituted Anilines in the Presence of Aromatic Additives," J. Phys. Chem., vol. 94 (1990) pp. 7716–7721.

Y. Wei et al., "Kinetics and Activation Parameters of Electrochemical Polymerization of 3–Alkylthiophenes in the Presence of Various Aromatic Additives," J. Phys. Chem., vol. 97 (1993) pp. 12842–12847.

Y. Wei et al., "A Study of the Mechanism of Aniline Polymerization," J. Polym. Sci.: Part A: Polym. Chem., vol. 27 (1989) pp. 2385–2396.

Y. Wei et al., "Effects of p–Aminodiphenylamine on Electrochemical Polymerization of Aniline," *J. Polym. Sci.: Part C: Polym. Lett.*, vol. 28 (1990) pp. 81–87.

Y. Wei et al., "A New Method for Preparation of Electrically Conductive Polythiophenes," *J. Polym. Sci.: Part C.: Polym. Lett.*, vol. 28 (1990), pp. 219–225.

Y. Wei et al., "Chemical and Electrochemical Copolymerization of Aniline with Alkyl Ring–Substituted Anilines," *Macromolecules*, vol. 23 (1990) pp. 758–764.

Y. Wei et al., "An Open–Circuit–Potential Study of the Chemical Polymerization of Aniline and Effect of Additives," *Polym. Prepr.*, vol. 35 (1) (1994) pp. 242–243.

M. Angelopoulus, et al., "Polyaniline: Solutions, Films and Oxidation State", *Mol. Cryst. Liq. Cryst.*, vol. 160, pp. 151–163, (1988).

S. Nešpůrek, "Photoelectric Properties of Linear Oligoaniline Derivatives", *Czech. J. Phys.*, vol. B 23, pp. 368–390, (1973).

F. Muzalewski, et al., "Electronic Absorption Spectra of Aromatic Schiff Bases. Part II*. Terephthaldehyde Derivatives", *Polish J. Chem.*, vol. 55, pp. 565–572, (1981).

V. Hádek, et al., "Electric and Magnetic Properties of Organic Semiconductors. Temperature Dependence of the Thermo–E.M.F. of Donor–Acceptor Complexes of Substituted Oligomeric Leucobases of Polyaniline Type With Iodine", *Collection Czechoslov. Chem. Commun.*, vol. 32, pp. 1118–1124, (1967).

* cited by examiner

END-FUNCTIONALIZED ANILINE-BASED OLIGOMERS, CORROSION-RESISTANT COPOLYMERS AND METHODS OF MAKING THE SAME

CROSS-REFERENCE TO RELATED APPLICATIONS

This application is a continuation of PCT/US96/16773, filed Oct. 18, 1996 and further claims the benefit of U.S. Provisional Applications Nos. 60/013,992, filed Mar. 20, 1996 and 60/005,731, filed Oct. 20, 1995. The entire disclosures of U.S. Provisional Applications Nos. 60/013,992 and 60/005,731 and of PCT/US96/16773, each as filed, are incorporated herein by reference.

BACKGROUND OF THE INVENTION

To impart corrosion-resistant properties to the surface of substrates subject to corrosion, such as metals, typically, the surface is coated with chromium-containing compounds. However, chromium-containing compounds present concerns regarding adverse health and environmental effects. The use of electroactive organic polymers as corrosion-inhibiting coatings has been explored as a potential replacement for chromium-containing compounds. One such polymer is polyaniline which can be prepared by oxidative polymerization of inexpensive aniline and which has a relatively good solubility for solution-coating applications.

Polyaniline in its completely oxidized form is known as pernigraniline, and in its fully reduced form as leucoemeraldine. When there is an equal fraction of oxidized and reduced units in the polymer, it is referred to as emeraldine. Upon doping the emeraldine base with a protonic acid such as hydrochloric acid, the emeraldine base exhibits moderate electric conductivity of about 10 S/cm.

It has also been shown that the non-conductive base form of polyaniline as a coating on cold-rolled steel (CRS) offers good corrosion protection. Small amine compounds also have long been used as corrosion inhibitors.

Oligomeric aromatic amines with amino-terminated end groups are of interest in the polymer field due to their use as monomers for preparing polyamides, polyimides and epoxy polymers. The synthesis of amino-terminated oligomers via conventional routes, when possible, is often very complicated. n,n'-bis(4'-aminophenyl)-1,4-phenylenediamine, a reduced form of n,n'-bis(4'-aminophenyl)-1,4-quinonenediimine has been synthesized by catalytic hydrogenation of n,n'-bis(4'-nitrophenyl)-1,4-phenylenediamine and was used as a trimer of aniline in elucidating the structure-semiconductivity relationship of aniline oligomers. In addition, another method was developed for preparing this oligomer to use it as a building block for achieving a total unambiguous synthesis of polyaniline by way of Schiff base chemistry. Both of these methods involve multiple synthetic steps and reduction of the nitro groups in the precursors. As such, it is difficult to apply these methods generally for synthesizing polyaniline and its derivatives, or for using in industrial applications.

As described in U.S. Pat. No. 4,920,517 of Yen Wei, herein incorporated by reference, aniline polymerization is undertaken by using a small amount of an initiator additive, such as 1,4-phenylenediamine, 1,4-aminodiphenylamine, n,n'-diphenylhydrazine, benzidine and the like. These additives drastically increased the rate of the oxidative polymerization of the aniline monomers. The growth of polymer chains is achieved via electrophilic aromatic substitution on neutral monomers by the oxidized growing polymer chain ends. The polymerization process is neither a classical step nor a classical chain polymerization, but is more of a combination of these processes. The additives function as a chain initiator and the molecular weight of polyaniline can be modified by varying the amount of initiator.

SUMMARY OF THE INVENTION

The invention includes a method of forming an oligomer from monomers of Formula I:

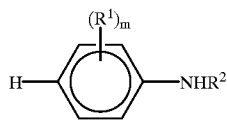

(I)

wherein $R^1$ and $R^2$ are independently selected from the group consisting of —H, —OH, —COOH, halogen, —NO$_2$, —NH$_2$, and substituted and unsubstituted alkyl, substituted and unsubstituted alkoxy and substituted and unsubstituted aryl groups; $R^1$ substitutions being ortho or meta to the NHR$^2$ group; and m is 0 to 4. The method comprises reacting the monomer of Formula (I), or a derivative or a water-soluble salt thereof, with greater than 10 mole percent of an initiator, in the presence of a chemical oxidant and/or an applied electrochemical potential. The initiator comprises a substituted or unsubstituted aromatic amine which has a lower oxidation potential than the monomer of Formula I and which is capable of being incorporated in a chain resulting from the reaction, wherein the oligomer has a molecular weight of less than 2300.

The invention also includes a method of forming an end-functionalized polymer from a monomer selected from the group consisting of compounds of Formula (III):

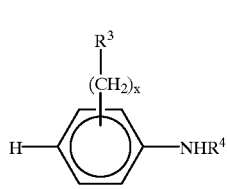

(III)

wherein $R^3$ is selected from the group consisting of —H, —OH, COOH, lower alkoxy, alkyl, aryl, halogen, —NO$_2$, and —NH$_2$, with substitutions being ortho or meta to the amine group; $R^4$ is hydrogen or lower alkyl; and x is 0 to 4, derivatives of compounds of Formula (III), and salts of Formula (III). The method includes the steps of reacting the monomer with an initiator, in the presence of a chemical oxidant and/or an applied electrochemical potential to form a polymer. The initiator comprises a substituted or unsubstituted aromatic amine which has a lower oxidation potential than the monomer and which is capable of being incorporated in the polymer chain resulting from the polymerization reaction. The polymer is converted to its base form, and reacted in its base form with an organic aldehyde to form an end-functionalized polymer, wherein amine end groups of the polymer are converted to imine end groups in the end-functionalized polymer.

The invention additionally includes a method of forming a corrosion-resistant composition comprising a corrosion resistant copolymer, the method comprising copolymerizing a monomer and an oligomer selected from the group consisting of oligomers having the following formula:

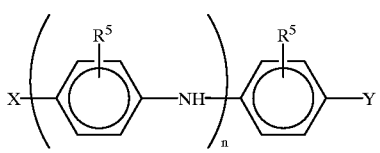

(IV)

wherein X and Y are independently selected from the group consisting of H, —$NH_2$, —$C_6H_4NH_2$, —$OC_6H_4NH_2$, alkyl, aryl, OH and $OR^5$; $R^5$ is selected from the group consisting of H, —OH, —COOH, alkyl, aryl, alkoxy, halogen, $NO_2$ and —$NH_2$; and n is from about 2 to about 40, derivatives of the oligomers of Formula (IV), salts of the oligomers of Formula (IV), and undoped or doped oligomers of Formula (IV) with Lewis or protonic acids, or fullerenes.

A method of forming a corrosion-resistant substrate is also within the invention. The method comprises coating at least one surface of the substrate with a composition comprising a corrosion-resistant oligomer selected from the group consisting of oligomers having the following formula:

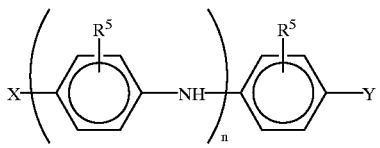

(IV)

wherein X and Y are independently selected from the group consisting of H, —$NH_2$, —$C_6H_4NH_2$, —$OC_6H_4NH_2$, alkyl, aryl, OH and $OR^5$; $R^5$ is selected from the group consisting of H, —OH, —COOH, alkyl, aryl, alkoxy, halogen, $NO_2$ and —$NH_2$; and n is from about 2 to about 400, derivatives of the oligomers of Formula (IV), and salts of the oligomers of Formula (IV).

The invention further includes a corrosion-resistant composition, comprising an oligomer selected from the group consisting of oligomers having the following formula:

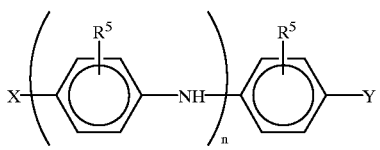

(IV)

wherein X and Y are independently selected from the group consisting of H, —$NH_2$, —$C_6H_4NH_2$, —$OC_6H_4NH_2$, alkyl, aryl, —H and $OR^5$; $R^5$ is selected from the group consisting of H, —OH, —COOH, alkyl, aryl, alkoxy, halogen, $NO_2$ and —$NH_2$; and n is from about 2 to about 400, derivatives of oligomers of Formula (IV), and salts of the oligomers of Formula (IV).

BRIEF DESCRIPTION OF THE SEVERAL VIEWS OF THE DRAWINGS

The following description of the preferred embodiments of the invention, will be better understood when read in conjunction with the appended drawings. For the purpose of illustrating and understanding the invention, there are shown in the drawings graphical data which will assist in understanding the invention. It should be understood, however, that the invention is not limited to the precise data shown in the graphical representations. In the drawings.

DETAILED DESCRIPTION OF THE INVENTION

Figure 1:
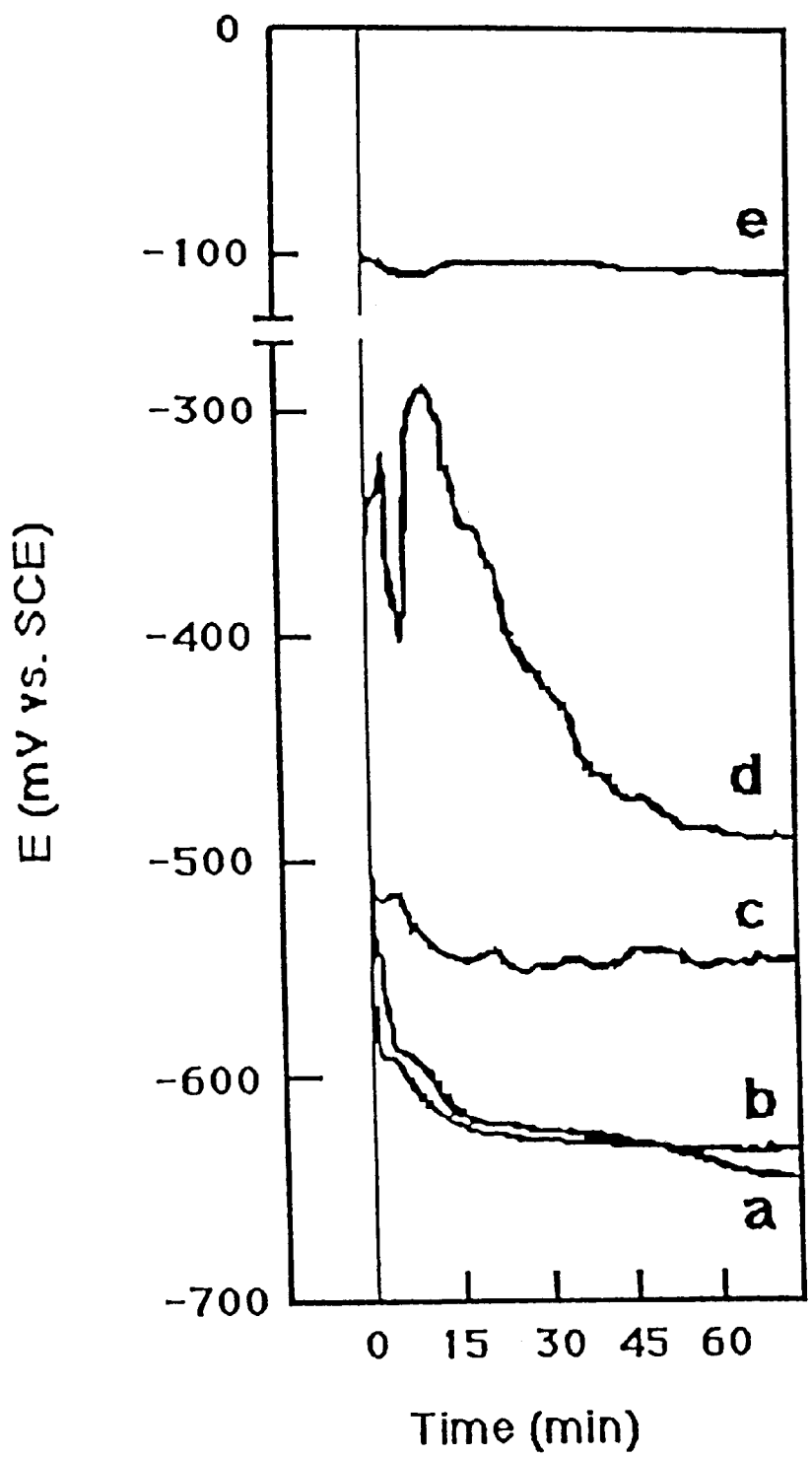
FIG. 1 is a graphical representation of corrosion potential ($E_{corr}$) against time for CRS coupons coated with various materials as shown in FIG. 1.

The present invention relates to the field of oligomers of aniline and their derivatives, end-functionalized oligomers of aniline and their derivatives, and the use of such oligomers as monomers for curing corrosion resistant coatings and for forming corrosion-resistant copolymers.

It has now been discovered that by using a high initiator:aniline ratio, more soluble and processible oligomers, and oligomers with specialized end groups can be obtained. For example, by using a ratio of 1:2 of 1,4-phenylenediamine to aniline, the trimer species n,n'-bis(4'-aminophenyl)-1,4-quinonenediimine can be formed in an appreciable yield. Both amino end-groups in 1,4-phenylenediamine can react with aniline monomers.

Further, by providing low molecular weight oligomers, the shorter chain length provides primary amine end group content which is higher than that of standard polyaniline which produces good solubility and excellent processing property.

In addition to discovering a simplified and reproducible method for synthesizing and/or derivatizing aniline oligomers, it has been discovered that using the oligomers to form coatings provides substantial anti-corrosive effects on surfaces such as CRS in comparison with use of chromium-coated surfaces and typical polyaniline-coated surfaces.

Aniline-based oligomers and polymers having molecular weights of preferably from about 2000 to about 200,000 can be synthesized according to the method of the present invention. The preferred low molecular weight oligomers, preferably having a molecular weight of from about 250 to about 2300 including specialized trimers of aniline and aniline derivatives are of particular use in forming end-functionalized oligomers and trimers, for forming corrosion resistant coatings, and for polymerizing with other monomers for various applications (including forming corrosion-resistant copolymers).

The preferred oligomers are formed by reacting an aniline-based monomer, or the salt or derivative thereof, with an initiator in the presence of a chemical oxidant and/or an applied electrochemical potential. Such electrochemical reactions are described in U.S. Pat. No. 4,940,517. Preferably, a chemical oxidant and chemical synthesis is used, however, it should be understood that the scope of the invention is not limited to use of chemical oxidants.

Suitable monomers for use in forming the oligomers include monomers having Formula (I) below and the derivatives and water soluble salts thereof.

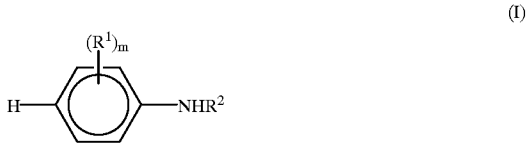

(I)

wherein $R^1$ and $R^2$ are independently selected from the group consisting of —H, —OH, —COOH, halogen, —$NO_2$, —NH$_2$, and substituted and unsubstituted alkyl, substituted and unsubstituted alkoxy and substituted and unsubstitued aryl groups; R$^1$ substitutions being ortho or meta to the NHR$^2$ group; and m is 0 to 4. The alkyl groups and alkoxy groups may be straight or branched chain, and should preferably be from about 1 to 20, and preferably from 1 to 10 carbon atoms and may be substituted randomly with halogen, fluorine, hydroxy, carboxy, amine, nitro and similar radicals. In addition, the compounds may be derivatized or converted to their salt form according to ordinary methods. Other similar aniline-based monomers which may be used for forming the oligomers will be apparent, based on this disclosure, to those skilled in the art.

Examples of suitable monomers include aniline, methylaniline, meta-toluidine, acetanilide, nitroaniline, n,n-dimethylaniline, methoxyaniline, dipropylaniline, and similar compounds and mixtures thereof.

The monomer, or its derivative or salt, is preferably reacted with an initiator in the presence of a chemical oxidant. In order to form preferred low molecular weight oligomers having molecular weights of from about 250 to about 2300, and in particularly dimers, trimers, tetramers, hexomers and the like from the monomer, the amount of initiator used should be greater than 10 mole percent of the amount of monomer. It is preferred that for very low molecular weight monomers and for producing a more uniform molecular weight distribution, the initiator is present in an amount of at least 10 mole %, and preferably in an amount of from about 10 mole % to about 50 mole % or more. For generating higher molecular weight oligomers and polymers, having molecular weights of from about 2,000 to about 200,000, for forming end-functionalized oligomers in accordance with another aspect of the invention, the initiator may be present in amounts of from about 0.1 to 10 mole %, and then end-functionalized as described further below.

The initiator is preferably another organic amine, and more preferably, an aniline-based compound and or low molecular weight oligomer. The initiators should have an oxidation potential lower than the monomer and should be capable of being incorporated in the chain resulting from the reaction, for example, as an integral part of the structural backbone. By becoming part of the structure, the resulting oligomers are not contaminated by extraneous moieties or other catalytic components used in prior art oligomeric and polymeric synthesis.

The initiator is preferably selected from the group consisting of compounds according to Formula (II) below, precursors of the compounds having Formula (II), salts of the compounds having Formula (II), and derivatives of the compounds having Formula (II).

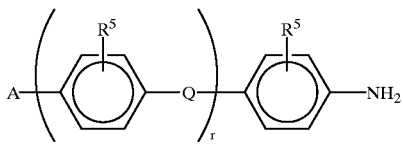

(II)

wherein A is selected from the group consisting of H, —NH$_2$, —C$_6$H$_4$NH$_2$, —OC$_6$H$_4$NH$_2$, alkyl, aryl, —SR$^1$, —OH and —COOH, R$^5$ is selected from the group consisting of H, —OH, —COOH, alkyl, aryl, alkoxy, halogen, NO$_2$ and —NH$_2$; Q is —NH, lower aminoalkyl, —O—, or —S—, and r is from about 0 to about 7, provided that when r is 0, A is not H or lower alkyl. Precursors or the fully or partially oxidized derivative forms of the compounds of Formula (II) may be used including, for example, the oxidized form of p-aminodiphenylamine, as shown below, may be used:

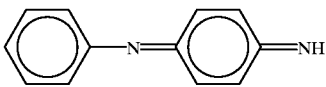

or the partially oxidized tetramer aniline:

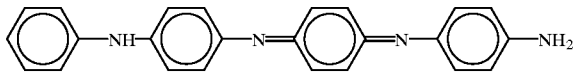

Preferred initiators include 1,4-phenylenediamine, dimers such as n,n'-diphenylenehydrazine, benzidine (n,n'-diphenylenehydrazine is a precursor which is believed to rearrange to form benzidine), n-phenyl-1,4-phenylenediamine, p-phenoxyaniline, p-phenylenediamine, and similar compounds which should be apparent to those skilled in the art, based on this disclosure. Particularly preferred for use with an aniline monomer are 1,4-phenylenediamine and n-phenyl-1,4-phenylenediamine.

The chemical oxidants may be any of a number of oxidizing agents. While strong oxidants are typically required with prior art polyaniline polymerization reactions, oligomers according to the present invention may be formed by using any oxidant, including weak oxidants such as oxygen gas to produce a reasonable yield and reaction rate. Suitable oxidants for use with the method of the present invention include, sulfate, chromate, chlorate, vanadate, ferricyanide with Na$^+$, K$^+$, or NH$_4^+$ as counter ions, peroxide, and oxygen. Preferably, the oxidizing agent is ammonium persulfate ((NH$_4$)$_2$S$_2$O$_8$). However, other suitable oxidizing agents will be apparent to one skilled in the art based on this disclosure. The oxidant should be provided in accordance with an oxidant to monomer ratio of from about 0.1:1 to 2:1, preferably from about 1:1 to about 1.25:1.

The yield, particularly when forming low molecular weight oligomers is very dependent upon the amount of oxidant used in comparison with the amount of monomer. If the oxidant to monomer ratio is about 1:1, the yield is significantly higher than if the ratio of oxidant to monomer is 1:2 as illustrated in the experimental Examples below.

The reaction is preferably carried out in a solvent medium and at atmospheric pressure. The temperature for forming the oligomers according to the present invention can vary widely from about –5° C. to about 60° C., depending upon the particular purity and reaction rate which must be achieved. For forming low molecular weight oligomers, and to prevent unwanted side reactions, the temperature is preferably as low as possible and preferably from about –5° C. to about 5° C.

Solvents which may be used in the present oligomeric reaction include water, solvents which are miscible in water, such as ketones, ethers, nitrites and protonic acids, organic solvents not miscible in water such as carbon tetrachloride and other hydrocarbon species, and mixtures thereof. The solvents should not be oxidizable in the reaction mixture. Preferred protonic acids for use with the present invention include hydrochloric acid (HCl), sulfuric acid (H$_2$SO$_4$), nitric acid (HNO$_3$), perchloric acid (HClO$_4$), phosphoric pentafluoric acid (HPF$_5$), and borotetrafluoric acid (HBF$_4$), and organic acids, such as alkyl or aryl sulfonic acids and trifluoroacetic acid, and polymeric acids. Most preferred for forming low molecular weight oligomers such as trimers and tetramers is hydrochloric acid, sulfuric acid, sulfonic acids and trifluoroacetic acid. The concentration of acid depends on the final pH of the reaction solution including the monomer, oxidant, solvent and acid which is preferably in the acidic range, and more preferably from −1 to 2 when using inorganic acids in aqueous media.

While not wishing to be bound by any particular theory, the following reaction equation is believed to apply for synthesis of low molecular weight oligomers such as trimers, tetramers and the like in accordance with the present invention:

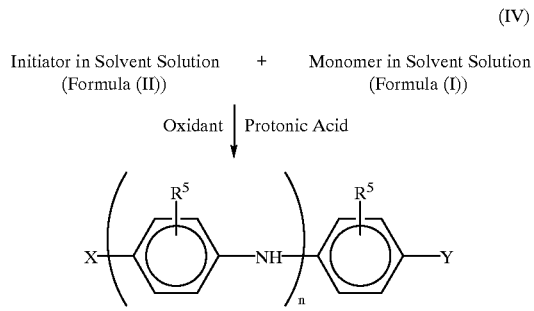

(IV)

wherein X and Y are independently selected from the group consisting of H, —$NH_2$, —$C_6H_4NH_2$, —$OC_6H_4NH_2$, alkyl, aryl, OH and $OR^5$; $R^5$ is selected from the group consisting of H, —OH, —COOH, alkyl, aryl, alkoxy, halogen, $NO_2$ and —$NH_2$; and n is from about 4 to about 400. Derivatives and salts of these compounds are also believed to be derived from this mechanism.

The oligomer formed may be further converted to a derivative form, which for the purposes of this application includes the oligomer in its fully oxidized, fully reduced or partially oxidized forms. The oligomer may be oxidized by converting the oligomer to its base form. The oligomer is then reacted in its base form with any suitable organic aldehyde, such as formaldehyde and similar compounds to form an end-functionalized oligomer.

The method for forming an end-functionalized polymer in accordance with the present invention includes reacting an aniline-based monomer such as, for example, the monomers of Formula (III) below, with an initiator, and in the presence of a chemical oxidant and/or an applied electrochemical potential to form an oligomer or polymer, depending upon the amount of initiator and the reaction conditions as discussed above. The initiator may be a substituted or unsubstituted aromatic amine which has a lower oxidation potential than the monomer and which is capable of being incorporated in the polymer chain resulting from the polymerization reaction. The initiator and oxidant may be the same as those discussed above, and the electrochemical procedure the same as that described in U.S. Pat. No. 4,940,517.

(III)

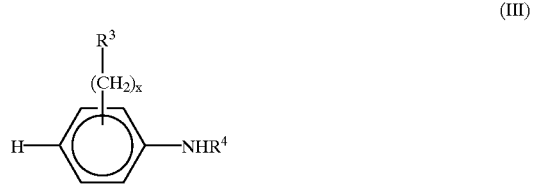

wherein $R^3$ is selected from the group consisting of —H, —OH, COOH, lower alkoxy, alkyl, aryl, halogen, —$NO_2$, and —$NH_2$, with substitutions being ortho or meta to the amine group; $R^4$ is hydrogen or lower alkyl; and x is 0 to 4. The monomer may also include derivatives of monomers of Formula (III) including the monomer in its various oxidized and reduced states, and salts of the monomer of Formula (III). The reaction conditions are largely the same as those describe above for synthesizing the oligomer.

The resulting polymer or oligomer is then converted to its base form and reacted, in its base form with an aldehyde, such as formaldehyde and similar compounds.

In end-functionalizing, it is believed that the reaction mechanism may be exemplified as described below, for example, but the invention should not be considered limited by such proposed mechanism. In a model reaction, aniline having two $NH_2$ groups in the para- position reacts in the presence of formaldehyde and one of the hydrogens in the $NH_2$ group is dropped. In its place, a double bond forms between the N and a CH— group bound to a phenyl group on either side of the molecule. In this manner, benzaldehyde is formed. In the oligomer synthesis, the oligomer reacts in the presence of solvent such as tetrahydrofuran and formaldehyde with ethanol and stirring to form a similar structure in which the terminal hydrogens of the oligomer are converted to the N=CH-phenyl groups on each end. In this manner, the end-capped oligomer is formed.

The present invention takes advantage of the unexpectedly improved corrosion properties of the oligomers and end-functionalized oligomers and polymers derived therefrom by including a method of forming a corrosion-resistant composition. The composition includes a corrosion resistant copolymer which may be formed by compolymerizing a monomer and an oligomer selected from the group consisting of oligomers having the following formula:

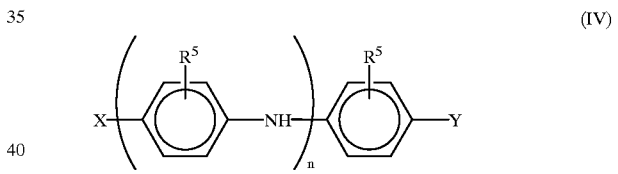

(IV)

wherein X and Y are independently selected from the group consisting of H, —$NH_2$, —$C_6H_4NH_2$, —$OC_6H_4NH_2$, alkyl, aryl, OH and OR; $R^5$ is selected from the group consisting of H, —OH, —COOH, alkyl, aryl, alkoxy, halogen, $NO_2$ and —$NH_2$; and n is from about 2 to about 40. Derivatives, such as the various oxidized and reduced states of the oligomers of Formula (IV), salts of the oligomers of Formula (IV), and undoped or doped oligomers of Formula (IV) with Lewis or protonic acids, or fullerenes are also useful. The doped oligomers, doped with either $Zn(NO_3)_2$ or HCl or similar compounds, provide increased corrosion-resistant properties. It has also been found that by doping the oligomers with fullerenes (for example, from about $C_{60}$ to about $C_{70}$), provide conductivities to the oligomeric or polymeric anilines of about $10^{-4}$ S/cm. Such fullerenes can be used as dopants in amounts of only about 1 mol % of the oligomer or polymer.

In a preferred embodiment, the monomer and the oligomer are copolymerized by various copolymerization methods such as condensation, and the like, to provide various commercially useful corrosion-resistant polymers of, for example, the polyamide, polyurethane, polyimide or epoxy-type. In addition, various configurations such as star, comb or other shape polymer configurations are possible using different monomer reactions. Further, cross-linked systems may also formed by providing the novel oligomers as additives in place of traditional cross-linking agents for polymer systems such as cross-linked epoxy.

A monomer and the above-described oligomer may be copolymerized by a condensation reaction and the copolymer is a copolymer of the oligomer and a functionalized or unfunctionalized monomer such as, for example, diacids, diacid halides, diisocyanates, diepoxides and similar compounds.

For the oligomer according to Formula (IV) when X=Y=NH$_2$, and a copolymer according to the following formula can be produced by standard polymerization procedures:

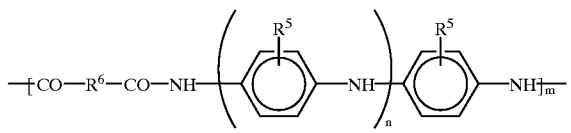

(V)

wherein m is from 1 to 10,000 and $R^6$ is selected from the group consisting of $(CH_2)_6$, phenyl, substituted or unsubstituted alkyl or aryl groups of preferably from about 1–20 carbon atoms, and saturated or unsaturated alkyl groups of preferably from about 1–20 carbon atoms, and similar radicals.

If an oligomer according to Formula (IV) is used and X=Y=NH$_2$, a copolymer according to the following formula may be formed using the polymerization techniques as described above:

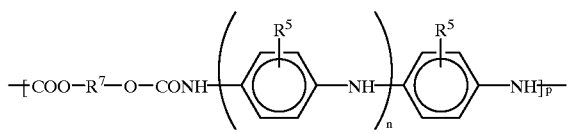

(VI)

wherein p is from 1 to 10,000 and $R^7$ is the same as $R^6$ above.

Copolymers according to the following formula may also be synthesized from the above-described oligomers.

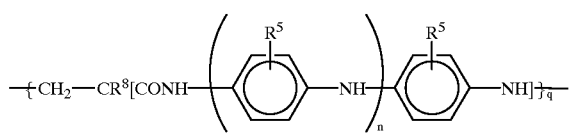

(VII)

wherein q is from 1 to $10^6$ and $R^8$ is the same as $R^6$.

In forming a specialty structure polymer, such as a star-polymer, for example, a monomer having the formula $R^9(COCl)_x$ may be polymerized with the oligomers and a copolymer having the following formula derived:

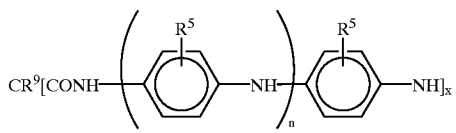

(VIII)

wherein $R^9$ is selected from the group consisting of saturated or unsaturated alkyl, saturated or unsaturated cycloalkyl, phenyl and substituted and unsubstituted aryl, and x is 1 to 4.

It will be apparent to those skilled in the art that the possibilities of forming various corrosion-resistant polymers from the oligomers, either doped or undoped are varied and the invention should not be interpreted as limited to the specific exemplary copolymers shown above.

The invention also includes a method of forming a corrosion-resistant substrate. The method includes coating at least one surface of a substrate such as metal, glass, silica, ceramic and the like which is vulnerable to corrosion, with a composition comprising a corrosion-resistant oligomer such as the corrosion-resistant oligomers described above. Preferably, a coating is formed which has a thickness of from about 0.01 to about 1000 microns depending upon the particular surface's corrosion rate in the uncoated state. Preferably, the corrosion-resistant oligomer is doped with either $Zn(NO_3)_2$ or hydrochloric acid. The corrosion-resistant oligomers as described above may be further copolymerized with compatible monomers, such as those described above for forming the composition and similar compounds, to form a corrosion-resistant copolymer.

The composition may be formed by using the corrosion-resistant oligomer to cure an epoxy resin. The epoxy resin should be cured with the oligomer at a temperature preferably in excess of 100° C., but the temperature should remain below the degradation temperature of the polymer. The oligomer may also be doped as described above prior to curing the epoxy compound. These coatings, as demonstrated below in the Examples, and particularly the doped compounds, represent significantly improved corrosion-resistant properties in comparison with conventional polymeric polyaniline and chromium coated compounds.

A corrosion-resistant composition is also provided in the invention which includes oligomers, or polymers, such as those of Formula (IV) above, wherein n is from 4 to about 400. Such oligomers or polymers show improved corrosion-resistance as do their derivatives in the various oxidized states, and salts of such oligomers or polymers. The molecular weight of the corrosion-resistant oligomers or polymers is preferably from about 200 to about 4000. The oligomers and polymers may also be doped with compounds such as those noted above. The oligomers and polymers, in the doped or undoped condition, may be further copolymerized to form a corrosion-resistant copolymer.

The oligomers or polymers may also be provided to an epoxy or similar resin to heat cure to form a corrosion-resistant composition which may or may not be doped with the above-described compounds.

The invention will now be described in more detail with respect to the following specific, non-limiting examples:

EXAMPLE 1

Aniline Oligomer Synthesis:

Freshly distilled aniline in the amount of 4.75 g (51 mmol) and 0.25 g (2.3 mmol) of 1,4-phenylenediamine were dissolved in 250 ml of 1M hydrochloric acid (aqueous) to form a monomer solution, and the solution was cooled to below 5° C. in an ice bath. A solution of 3 g (13 mmol) of $(NH_4)_2S_2O_8$ in 150 ml of 1M hydrochloric acid (aqueous), precooled to below 5° C., was poured into the monomer solution with vigorous stirring and allowed to react. The reaction proceeded at 0–5° C. for about 1.5 h. A blue precipitate was formed and collected by filtration under reduced pressure and washed thoroughly with distilled water until the filtrate formed no precipitation with silver nitrate solution. The product was then treated with 0.1M aqueous ammonia at room temperature for 3 h. Upon filtering and drying under vacuum at 50° C. for 48 h, a blue powder of amino-terminated oligomer in the emeraldine base form was obtained. The number-average molecular weight was found to be about 2300 based on GPC measurements with polystyrene calibration.

EXAMPLE 2

Aniline Trimer Synthesis Procedure:

1,4-phenylenediamine in the amount of 0.86 g (8 mmol) was dissolved in a solution of 100 ml of aqueous 1M hydrochloric acid and 40 ml ethanol. The solution was then cooled to about −5° C. in a NaCl-crushed ice bath. To this solution, 1.8 g (8 mmol) of ammonium persulfate was added in one portion with stirring under air. After about 5 minutes, the reaction solution became dark brown and 1.5 ml (16 mmol) of doubly distilled aniline was added quickly. Several minutes later, a blue particle suspension was formed and the reaction mixture was stirred vigorously for an additional 30 min.

The solid product, n,n'-bis(4'aminophenyl)-1,4-quinonenediimine, was collected by filtration through a Buchner funnel under reduced pressure and washed with 30 ml of 1M hydrochloric acid followed by 80 ml of distilled water. The product was then treated with 40 ml of 1M aqueous solution of ammonium hydroxide for 1–2 h. The mixture was filtered under reduced pressure and the remaining solid was washed with distilled water until the filtrate was neutralized. Upon drying at 40° C. over night under vacuum, 0.93 g of product was obtained as a blue powder with a 40% yield. The product was then purified by dissolving in tetrahydrofuran followed by column chromatography over silica gel with a 1:3 (volume ratio) mixture of ethyl acetate/hexane or diethyl ether alone as a diluent.

EXAMPLES 3–6

For Examples 3–6, the same procedure used for forming the trimer n,n'-bis(4'aminophenyl)-1,4-quinonenediimine above from 1-phenylenediamine of Example 2 was used to synthesize derivatives of the trimer in accordance with the following reaction scheme and compounds:

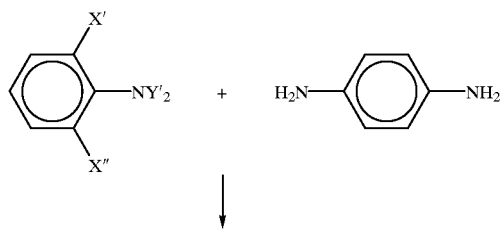

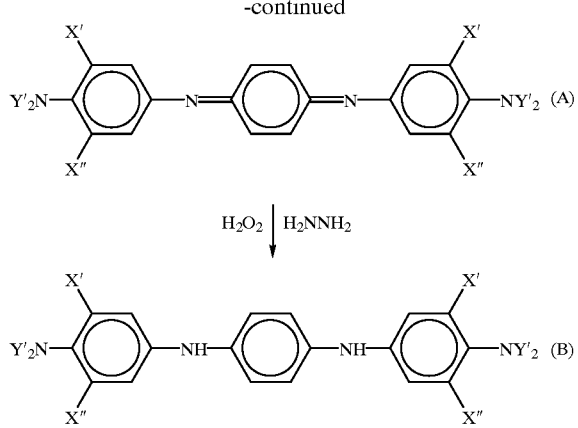

According to the above reaction mechanism, in Example 2 above, $X'=X''=Y'=H$ and the product is formed in accordance with Formula A. In Example 3, for both the reactant and product according to Formula A, $X'=CH_3$ and $X''=Y'=H$. In Example 4 for the reactant and product according to Formula A, $X'=X''=CH_3$ and $Y'=H'$ In Example 5 for the reactant and product according to Formula A, $X'=Cl$, $X''=Y'=H$. For Example 6, for the reactant and the product according to Formula A, $X'=X''=H$ and $Y=CH_3$.

In a subsequent reaction, the compound of Example 2 was reduced with hydrazine under a nitrogen atmosphere yielded a while solid which was characterized as n,n'-bis(4,-aminophenyl)-1,4-phenylenediamine having a melting point of 198° C. as expressed in Formula B, with $X'-X''=Y'=H$. The wavelength of maximum ultraviolet absorption (Maximum X) in dimethylformamide was 312, in tetrahydrofuran was 310 and in dichloromethane was 314. In comparison with the results shown in Table 1, it can be seen that the reduced form of the compound from Example 2 has a much lower Maximum X. It should be noted that this reduced form undergoes oxidation by air or by other oxidants such as hydrogen peroxide to regenerate the oxidized form of the compound.

EXAMPLES 7–10

The same procedure as that of Examples 2–4 and 6 was undertaken respectively in Examples 7–10, however, in the aniline trimer synthesis, 16 mmol of ammonium persulfate oxidant was added, such that the molar ratio of the ammonium persulfate to aniline or the aniline derivative of Example 2–5 was 1:1 instead of 1:2. The effect of the change in yield is shown in Table 1. All of the compounds of Examples 2–10 were characterized by infrared, electronic absorption, exact mass, and NMR spectroscopy and the results were consistent with the proposed structures. All of the trimers exhibited excellent solubility in most common organic solvents. The wavelengths of maximum ultraviolet absorption (Maximum λ) were measured in various solvents such as dimethylformamide (DMF), tetrahydrofuran (THF) and dichloromethane ($CH_2Cl_2$).

TABLE 1

| Compound Example Nos. | Additive/ Aniline Ratio[1] | Percentage Yield[2] 1:2 | Percentage Yield[2] 1:1 | Maximum λ (nm) DMF | Maximum λ (nm) THF | Maximum λ (nm) CH$_2$Cl$_2$ |
|---|---|---|---|---|---|---|
| 2 and 7 | 1:2 | 40 | 77 | 572 | 556 | 532 |
| 3 and 8 | 1:2 | 42 | 83 | 578 | 558 | 539 |
| 4 and 9 | 1:2 | 42 | 64 | 578 | 560 | 546 |
| 5 | 1:2 | 28 | — | 554 | 544 | 520 |
| 6 and 10 | 1:2 | 35 | 75 | 596 | 590 | 585 |
| 1 | 1:22 | 24[3] | — | 613[4] | — | — |
| polyaniline- emeraldine base (no additives) | — | 20[3] | — | 630[4] | — | — |

[1] approximate molar ratio of the additive, such as the 1,4-phenylenediamine of Example 2 to the aniline or substituted aniline used in each Example.
[2] approximate molar ratio of ammonium persulfate to aniline or substituted aniline used in each Example.
[3] ratio of 1:4
[4] measured in NMP solution

EXAMPLE 11

Coating Preparation:

A trimer-cured epoxy coating was made by first dissolving the 0.144 g (0.5 mmol) of the trimer synthesized in Example 2 in 2.0 ml of dimethylformamide. The solution was then combined with 0.17 g (0.5 mmol) epoxy resin in the form of bisphenol-A-diglycidyl ether from Dajac Lab. The epoxy used was Araldine® GY2600 from Ciba-Geigy. The solution was then spread on uncoated CRS coupons (measuring 2.54 cm×2.54 cm) from Akzo-Nobel Coatings in Columbus, Ohio. The coupons were initially prepared prior to use by polishing with fine, 400 Grit polishing paper from LECO Corp. (Number 183) followed by washing thoroughly with distilled water, acetone and ethanol. The coated coupons were cured at 120° C. for about 1 h. The coating thickness was about 130 μm.

The coated coupons and uncoated coupons were mounted as the working electrode in a standard corrosion test cell with two graphite rods of 6.15 mm diameter as counter electrodes, a saturated calomel reference electrode and a gas purge tube. When mounting the coated coupons, the coated side of the coupon was in direct contact with the electrolyte. The edges of the coupons were sealed with Elmers epoxy cement. Electrochemical measurements were made using an EG&G PAR 273 potentiostat/galvanostat at room temperature. The electrolyte was a 5 wt % aqueous solution of NaCl. The open circuit potential at equilibrium was taken as the corrosion potential ($E_{corr}$). The polarization resistance ($R_p$) as measured in ohm/cm$^2$ was measured by sweeping the applied potential from 20 mV below to 20 mV above the $E_{corr}$ at a scan rate of 0.2 mV/s. The Tafel plot was obtained by scanning potential from 250 mV below to 250 mV above the $E_{corr}$ at a scan rate of 0.2 mV/s. The corrosion current ($i_{corr}$) was determined by superimposing a straight line along the linear portion of the cathodic or anodic curve and extrapolating it through $E_{corr}$. The corrosion rate ($R_{corr}$) in milli-inches/year (MPY) was calculated using the equation:

$$R_{corr} = [0.13 i_{corr}(\text{equivalent weight})]/[(A)(d)]$$

where $R_{corr}$ is measured in MPY, equivalent weight is measured in g/equivalent, A is the area measured in cm$^2$ and d is the density measured in g/cm$^3$. The corrosion potential was measured and plotted against time as shown in FIG. 1.

Figure 2:
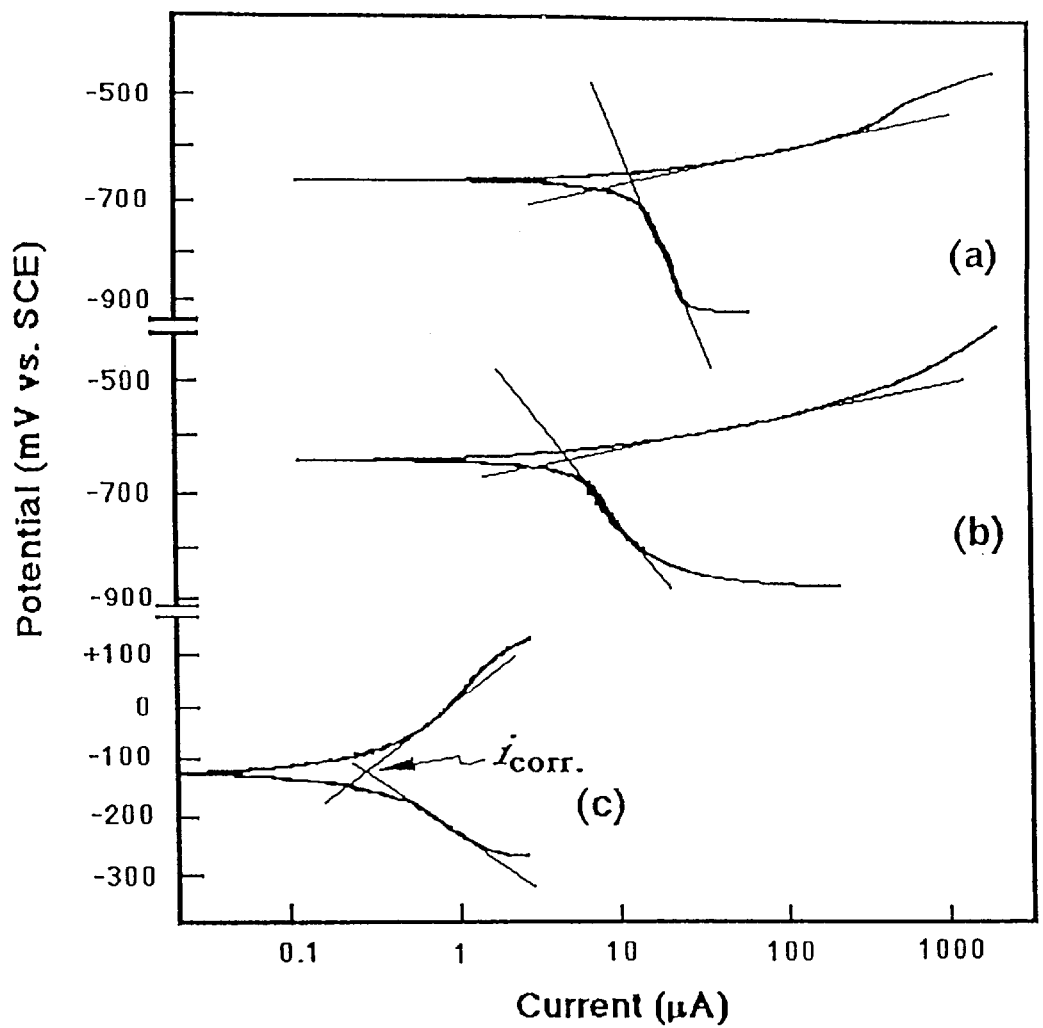
FIG. 2 is a graphical representation of corrosion current ($i_{corr}$) measured in $\mu A$ against corrosion potential (mV) for CRS coupons coated with various materials.

After about 60 min, the corrosion potential in the system became relatively stabilized. The plot of $E_{corr}$ v. time is shown in FIG. 1 for (a) an uncoated coupon; (b) a polyaniline-coated coupon as formed in Example 12; (c) a chromium primer-coated coupon; (d) a chromium primer-coated coupon also having a topcoat; and (e) an oligomer-coated coupon as formed in Example 13. FIG. 2 also includes a plot of corrosion current ($i_{corr}$) measured in μA against corrosion potential (mV), for determining corrosion rate ($R_{corr}$) measured in MPY for (a) an uncoated coupon; (b) a polyaniline-coated coupon as formed in Example 12; and (c) an oligomer-coated coupon as formed in Example 13.

EXAMPLE 12

Conventional polyaniline-emeraldine base fine powder was dissolved in an amount of from 1–2 wt % in HPLC grade 1-methyl-2-pyrrilidinone. The solution was cast dropwise onto uncoated CRS coupons as described in Example 11 and air dried for 48 h to give coatings of about 20–130 μm in thickness. Electrochemical analysis was undertaken on the coupons in the same manner as in Example 11 and the results of the $E_{corr}$ after 60 min are shown in FIG. 1.

EXAMPLE 13

The oligomers of Example 1, which exhibited higher solubility than the polyaniline in Example 5, were dissolved in a 10 wt % solution of 1-methyl-2-pyrrilidinone. The solution was combined with 10 wt % Araldine®GY2600 epoxy from Ciba-Geigy. The mixture was spread on uncoated CRS coupons and heated at 100° C. for 1 h. The thickness of the coating was about 100 μm. The electrochemical analysis was undertaken on the coupons in the same manner as in Example 11 and the results of the $E_{corr}$ after 60 min are shown in FIG. 1.

As FIGS. 1 and 2 and Examples 11–13 show, after 60 minutes, the corrosion potentials in all systems become relatively stabilized. The polyaniline-coated coupon shows a higher $E_{corr}$ value than the uncoated coupon in FIG. 1 after 60 minutes. However, it has a lower $E_{corr}$ than the coupons coated with chromium-containing primer and chromium-containing primer and topcoat. The oligomer-coated coupon exhibits a high corrosion potential of about −110 mV at 60 minutes. Even after a 5 h measurement, the potential remained at about −130 mV. Such a high $E_{corr}$ value suggests that the oligomer-coated coupon is very noble towards the electrochemical corrosion. The oligomer-coated coupon showed a polarization resistance ($R_p$) value of $1.7 \times 10^5$ ohm/cm$^2$ in 5 wt % NaCl, which is about two orders of magnitude greater than the uncoated coupon.

The Tafel plots of FIG. 2 show that the corrosion current ($i_{corr}$) for the oligomer-coated coupon is about 0.27 $\mu$A/cm which corresponds to a corrosion rate of about 0.13 MPY. This is significantly lower than the polyaniline-coated coupon where $i_{corr}$ is about 3 $\mu$A/cm2 and the corrosion rate is about 1.3 MPY. Further the uncoated coupons show an i of 10 $\mu$A/cm$^2$ with a corr corrosion rate of 4.3 MPY. As this data show, the oligomer-based coatings offer good corrosion protection and show a better anti-corrosion performance than conventional polyaniline. Similar results to those for the oligomer-cured epoxy coated coupons were found when testing trimer-cured epoxy coated coupons from Example 11.

EXAMPLE 14

1,4-phenylenediamine in an amount of 8.6 g ($7.96 \times 10^{-2}$ mole) and 14.8 g ($15.91 \times 10^{-2}$ mole) of aniline were dissolved in 1000 ml of 1M hydrochloric acid solution containing 200 ml ethanol or methanol. To the solution, 18 g ($7.89 \times 10^{-2}$ mole) of $(NH_2)_2S_2O_8$ was added after the solution was cooled to between 0–5° C. A densely blue precipitate was produced after stirring 5 minutes at 0–5° C. An exothermic reaction occurred such that the temperature of the solution increased to about 10° C. The temperature of the mixture dropped to 0° C. and its density became low as the reaction time proceeded. The precipitate was collected by filtration through a Buchner funnel under a reduced pressure and washed with 200 ml 1M hydrochloric acid aqueous solution after the reaction mixture was stirred at 0° C. for 1 h to form and hydrochloric acid-doped amino-capped trianiline. This material was then neutralized by 10% NH$_4$OH aqueous solution and was washed by a large amount of distilled water to form 6.5 g of amino-capped trianiline having a yield of 28.4%.

EXAMPLE 15

Using the same ratio of starting materials in Example 14, $(NH_4)_2S_2O_8$ was added to the soltuion of 1,4-phenylenediamine and aniline at −10° C. The temperature of the solution was slowly increased to −5° C. The yield of amino-capped trianiline was about the same as that produced in Example 14. However, the purity of the product improved.

EXAMPLE 16

The procedure of Example 15 was repeated except that the amount of $(NH_4)_2S_2O_8$ was doubled. Amino-capped trianiline was produced in an amount of 13 g with a yield of 56.7%.

EXAMPLE 17

The procedure of 15 was repeated except that the amount of $(NH_4)_2S_2O_8$ was tripled. Amino-capped trianiline was produced in an amount of 14.4 g with a yield of 62.8%.

EXAMPLE 18

The procedure of Example 16 was repeated except that the amount of methanol or ethanol was doubled. The amount of amino-capped trianiline was approximately the same as in Example 16, however, the purity was not as good as that from Example 16.

EXAMPLE 19

The procedure of Example 16 was repeated except that the amount of ethanol or methanol was replaced by 50 g NaCl as an anti-freeze component. The yield of amino-capped trianiline was approximately the same as in Example 16, however, the purity was improved from that of Example 16.

EXAMPLE 20

4,4'-diamino-diphenylamine sulfate in an amount of 23.65 g ($7.96 \times 10^{-2}$ mole) and 7.4 g ($7.96 \times 10^{-2}$ mole) of aniline were dissolved in 800 ml 1M hydrochloric acid aqueous solution containing 50–100 g NaCl. The solution of 200 ml 1M hydrochloric acid and 18 g of $(NH_4)_2S_2O_8$ ($7.89 \times 10^{-2}$ mole) was dropped into the solution at about 60 drops/minute after the above solution was cooled to −7° C. The reaction mixture was stirred for 1 h at −5° C. after the solution of $(NH_4)_2S_2O_8$ was added by dropping. The precipitate was collected by filtration through a Buchner funnel under a reduced pressure and washed with 400 ml 1M hydrochloric acid cooled to 0° C. producing a hydrochloric acid-doped amino-capped trianiline. This material was then neutralized with 10% NH$_4$OH aqueous solution and washed with a large amount of distilled water. The product formed was an amino-capped trianiline in an amount of 11.8 g and had a high purity. The yield was 52.5%.

EXAMPLE 21

The amino-capped trianiline of Example 20 was prepared in its reduced leucoemeraldine base form by using the powder of the oxidative state amino-capped trianiline by suspending 1 g of the powder and refluxing in 35% hydrazine solution (50 ml) for 4 hours under a nitrogen atmosphere. The reaction mixture was filtered under a nitrogen atmosphere and the crude product recrystallized twice in dehydrated ethyl alcohol containing a trace of 99% phenylhydrazine and 35% hydrazine consecutively under nitrogen. A white powder leucoemeraldine base was produced and dried in a vacuum.

EXAMPLE 22

A solution of 5 ml 36% hydrochloric acid and 10 ml H$_2$O was added to a solution containing 0.6 g oxidative state amino-capped trianiline prepared from Example 20 and 60 ml dimethylformamide. The mixture solution was stirred for 1 h at room temperature. The color of the mixture solution slowly darkened. Then 45 ml H$_2$O and 10 ml 30% NH$_4$OH was added to the dark mixture solution. The precipitate was filtered and washed by H$_2$O and ethanol in order. About 0.15 g insoluble powder was produced after drying at 80° C. for about 8 h.

EXAMPLE 23

An oligomeric polyaniline was synthesized by placing 4.75 (0.051 mol) distilled aniline and 0.25 g (0.0023 mol) 1,4-phenylenediamine in a flask cooled to −5° C. 350 ml of pre-cooled 1 M hydrochloric acid was slowly added to the flask and stirred. Ammonium persulfate was added in an amount of 3.04 g to 150 ml pre-cooled 1M hydrochloric acid in a separate flask. The clear oxidant solution was slowly added to the stirring mixture of aniline and 1,4-phenylenediamine. Within minutes, the solution mixture slowly turned from tinted light brown into a darkening blue solution finally ending as a thick dark blue-green precipitate. This precipitate was slowly filtered with low vacuum and the resulting polymer cake was left to dry over night. The cake was then thoroughly washed with approximately 2 liters of distilled water periodically testing the afterwash for sulfate ions using silver nitrate solution. After determining no sulfate ions were present, the cake was allowed to dry.

The product was then converted to its emeraldine base form by stirring in aqueous ammonia for at least 5 h before filtering adn allowing the fine blue powder to dry. Additional vacuum oven drying was performed at 60° C.

The synthesized emeraldine base oligomer in an amount of 0.2 g was slowly sprinkled over a 250 ml beaker containing 150 ml tetrahydrofuran in a BRANSON ultrasonic bath. The polyaniline solution was then transferred to a 500 ml flask with flux condenser and thermometer adaptor and heated with stirring to 60° C. in a heating bath. A separate solution of 1 g (0.0082 mol) p-hydroxybenzaldehyde in 50 ml absolute ethanol was prepared and slowly added via a dropping funnel to the polyaniline solution. The reaction was allowed to proceed for at least 3 days and then transferring the reaction mixture to a rotovap flask and stripping the solvent. The greenish blue powder was thoroughly ether washed and soxhlet extracted for at least 3 days with ether. The fully washed product was vacuum dried in an oven at 60° C. and characterized by NMR, Infrared, Ultraviolet, TGA, DSC, GPC, EA and x-ray spectroscopy. Reduction with sodium borohydride and lithium hydride was achieved by reflux with the endcapped polymer in dimethylformamide, cooling the mixture, pouring ethanol and then filtering, air drying, recrystallizing in methanol and characterizing the reduced base.

EXAMPLE 24

Aniline oligomers and trimers formed in accordance with the procedure of Examples 1 and 2 were used and converted to their base form. Standard polyaniline was also synthesized. GPC chromatography was carried out using NMP as solven and calibrated with monomdispersed polystyrene standard which molecular weight covered from 1,800 to 110,000. The relationship between the percentage content of the additives and the number-average molecular weight (Mn) was examined. It was determined that the molecular weight for the standard polyaniline method produced weights from about 2200 to about 4800 for the low molecular weight fraction and about 170,000 to 200,000 for the high molecular weight fraction. The Mn of the polyaniline formed in the conventional method, without the initiator, according to GPC, was 9,419 to 1,572,112. Using the same reaction conditions, the Mn of the oligomers formed with initiators in accordance with the present method were much lower. The Mn dropped below 10,000 when percentage content of initiator used was only about 2–3%. The results indicated that only small amounts of initiator was sufficient to control molecular weight.

The polyaniline formed in accordance with the present method also showed a narrower molecular weight distribution. The GPC analysis showed the molecular weight distribution of polyaniline without initiator and formed in accordance with standard methods was quite broad providing a value of 3.8. The molecular weight distribution increased and became narrower and narrower with increase amounts of initiator. The value also varied with additives. For oligomers formed with about 10 mole% 1,4-phenylenediamine, the value was 1.2. For oligomers formed with about 10 mole % of 1,4-phenylenediamine, the value was 1.7. The results showed that 1,4-phenylenediamine was the more effective initiator for adjusting molecular weight distribution in comparison with n-phenyl-1,4-phenylenediamine.

The results of the molecular weight distribution data for both initiators are shown below in Table 2:

TABLE 2

| | Molecular weight distribution | |
|---|---|---|
| Mole % Initiator | 1,4-phenylene-diamine | n-phenyl-1,4-penylene-diamine |
| 0 | 3.8 | 3.8 |
| 2 | 2.0 | 3.56 |
| 3 | 2.02 | — |
| 4 | 1.66 | — |
| 5 | 1.54 | 1.86 |
| 8 | 1.28 | 1.77 |
| 11 | 1.20 | — |
| 15 | 1.14 | 1.73 |
| 20 | 1.25 | 1.50 |
| 25 | 1.24 | — |
| 40 | 1.14 | — |

As the data revealed upon analysis, bimodel molecular weight distribution significantly decreased and approached monomodel distribution with increasing amounts of initiator. To determine reproducibility, an oligomer was synthesize in accordance with the procedure of Example 1 using 5 mol % 1,4-phenylenediamine and the Mn and Mw results, as well as the Mw/Mn results are shown in Table 3 below:

TABLE 3

| Mol % Initiator | Mn | Mw | Mw/Mn |
|---|---|---|---|
| 5 | 2164 | 2975 | 1.37 |
| 5 | 2097 | 2803 | 1.34 |
| 5 | 4534 | 6792 | 1.50 |
| 5 | 4722 | 7278 | 1.54 |
| 5 | 5534 | 9003 | 1.63 |
| 5 | 6862 | 11664 | 1.70 |

The conductivities were measured for various amounts of 1,4-phenylenediamine with washing with distsill water and without washing with large amounts of distilled water to remove oxidant residue and are shown below in Tables 4 (no washing) and Table 5 (washing).

TABLE 4

| Mol % Initiator | Conductivity (S/cm) | Log (conductivity) | Mn | Log (Mn) |
|---|---|---|---|---|
| 0 | 3.17 | 0.50 | 22491 | 4.35 |
| 5 | 0.023 | (1.64) | 6862 | 3.84 |
| 8 | 0.000888 | (3.05) | 6884 | 3.84 |
| 20 | $3.1 \times 10^{-5}$ | (4.51) | 4266 | 3.63 |
| 40 | $2.02 \times 10^{-5}$ | (4.69) | 4130 | 3.62 |

TABLE 5

| Mol % Initiator | Conductivity (S/cm) | Log (conductivity) | Mw | Log (Mw) |
|---|---|---|---|---|
| 0 | 2.07 | 0.32 | 790765 | 5.90 |
| 2 | 0.191 | (0.72) | 8650 | 3.94 |

TABLE 5-continued

| Mol % Initiator | Conductivity (S/cm) | Log (conductivity) | Mw | Log (Mw) |
|---|---|---|---|---|
| 3 | 0.072 | (1.14) | 5282 | 3.72 |
| 4 | 0.0212 | (1.67) | 5644 | 3.75 |
| 5 | 0.00625 | (2.20) | 2164 | 3.34 |
| 20 | 0.00015 | (3.82) | 1150 | 3.06 |
| 25 | $1.73 \times 10^{-5}$ | (4.76) | 916 | 2.96 |
| 40 | $1.32 \times 10^{-5}$ | (4.88) | 1349 | 3.13 |

In these examples, the Mn is the number average molecular weight and Mw is the weight-average molecular weight as determined according to conventional means. As the above data show, the conductivity and molecular weight increase except for the conductivity of a 5% dimer.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method of forming an oligomer from monomers of Formula I:

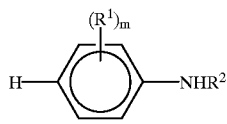
(I)

wherein $R^1$ and $R^2$ are independently selected from the group consisting of —H, —OH, —COOH, halogen, —NO$_2$, —NH$_2$, and substituted and unsubstituted alkyl, substituted and unsubstituted alkoxy and substituted and unsubstituted aryl groups; $R^1$ substitutions being ortho or meta to the —NHR$^2$ group; and m is 0 to 4, the method comprising:

reacting the monomer of Formula I, or a derivative or water-soluble salt thereof, with greater than 10 mole percent of an initiator, in the presence of a chemical oxidant and/or an applied electrochemical potential, said initiator comprising a substituted or unsubstituted aromatic amine that has a lower oxidation potential than the monomer of Formula I and which is capable of being incorporated in a chain resulting from the reaction, wherein the oligomer has a molecular weight of less than 2300, and is in an at least partially oxidized form; and converting the oligomer to its base form and reacting the base form of the oligomer with an organic aldehyde to form an end-functionalized oligomer, wherein amine end groups of the oligomer are converted to imine end groups in the end-functionalized oligomer.

2. The method according to claim 1, wherein the organic aldehyde is selected from the group consisting of R'—M where M is selected from the group consisting of H, —OH, NH$_2$, halogen, —COOH, —NO$_2$, —CHO, ketone, and R' is selected from the group consisting of saturated or unsaturated and substituted or unsubstituted alkyl groups, and saturated or unsaturated and substituted or unsubstituted aryl groups.

3. A method of forming an end-functionalized polymer or oligomer from a monomer selected from the group consisting of compounds of Formula III:

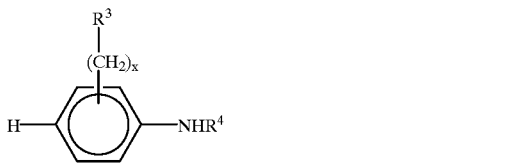
(III)

wherein $R^3$ is selected from the group consisting of —H, —OH, COOH, lower alkoxy, alkyl, aryl, halogen, —NO$_2$, and —NH$_2$, with substitutions being ortho or meta to the amine group; $R^4$ is hydrogen or lower alkyl; and x is 0 to 4, derivatives of compounds of Formula (III), and salts of Formula (III), the method comprising the steps of:
(a) reacting the monomer with an initiator, in the presence of a chemical oxidant and/or an applied electrochemical potential to form a polymer or oligomer, said initiator comprising a substituted or unsubstituted aromatic amine which has a lower oxidation potential than the monomer of Formula (III) and which is capable of being incorporated in the polymer chain resulting from the polymerization reaction;
(b) converting the polymer to its base form;
(c) reacting the polymer in its base form with an organic aldehyde to form an end-functionalized polymer, wherein amine end groups of the polymer are converted to imine end groups in the end-functionalized polymer.

4. A method of forming a corrosion-resistant composition comprising a corrosion resistant copolymer, the method comprising copolymerizing a monomer and an oligomer selected from the group consisting of oligomers having the following formula:

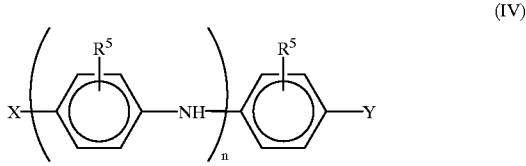
(IV)

wherein X and Y are independently selected from the group consisting of H, —NH$_2$, —C$_6$H$_4$NH$_2$, —OC$_6$H$_4$NH$_2$, alkyl, aryl, —OH and —OR$^5$; $R^5$ is selected from the group consisting of H, —OH, —COOH, alkyl, aryl, alkoxy, halogen, —NO$_2$ and —NH$_2$; and n is from about 2 to about 40, derivatives of the oligomers of Formula (IV), salts of the oligomers of Formula (IV), undoped or doped oligomers of Formula (IV) with Lewis or protonic acids, wherein the monomer and the oligomer are copolymerized by a condensation reaction and the copolymer is a copolymer of the oligomer and a functionalized or unfunctionalized monomer selected from the group consisting of a diacid, diacid halide, diisocyanate, and diepoxide.

5. The method according to claim 4, wherein X=Y=NH$_2$ and the copolymer has the formula:

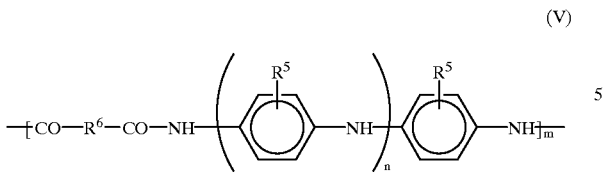

(V)

wherein m is from 1 to 10,000 and $R^6$ is selected from the group consisting of H, $(CH_2)_6$, phenyl, substituted or unsubsituted alkyl or aryl groups, and saturated or unsaturated alkyl groups.

6. The method according to claim 5, wherein $X=Y=NH_2$ and the copolymer has the formula:

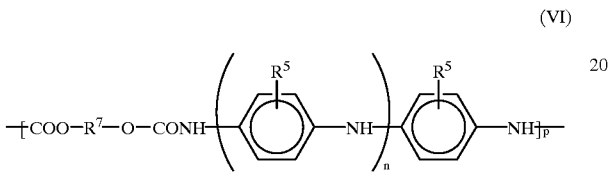

(VI)

wherein p is from 1 to 10,000 and $R^7$ is selected from the group consisting of H, $(CH_2)_6$, phenyl, substituted or unsubsituted alkyl or aryl groups, and saturated or unsaturated alkyl groups.

7. The method according to claim 4, wherein the copolymer has the formula:

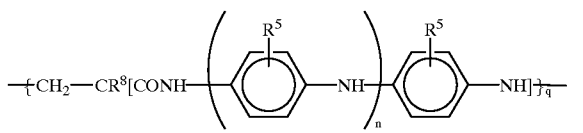

(VII)

wherein q is from 1 to $10^6$ and $R^8$ is selected from the group consisting of H, $(CH_2)_6$, phenyl, substituted or unsubsituted alkyl or aryl groups, and saturated or unsaturated alkyl groups.

8. The method according to claim 4, wherein the monomer has the formula $R^9(COCl)_x$ and the copolymer has the formula:

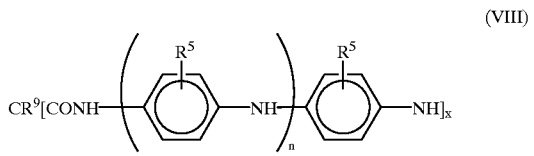

(VIII)

wherein $R^9$ is selected from the group consisting of saturated or unsaturated alkyl, saturated or unsaturated cycloalkyl, phenyl and substituted and unsubstituted aryl, and x is 1 to 4.

9. A method of forming a corrosion-resistant substrate comprising coating at least one surface of the substrate with a composition comprising a corrosion-resistant oligomer selected from the group consisting of oligomers having the following formula:

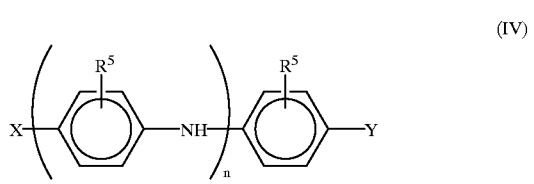

(IV)

wherein X and Y are independently selected from the group consisting of H, $—NH_2$, $—C_6H_4NH_2$, $—OC_6H_4NH_2$, alkyl, aryl, OH and $OR^5$; $R^5$ is selected from the group consisting of H, $—OH$, $—COOH$, alkyl, aryl, alkoxy, halogen, $NO_2$ and $—NH_2$; and n is from about 2 to about 400, derivatives of the oligomers of Formula (IV), and salts of the oligomer of Formula (IV).

10. The method according to claim 9, further comprising coating the substrate with the composition to form a coating layer having a thickness of from about 0.1 to 1,000 microns.

11. The method according to claim 9, further comprising doping the oligomer with $Zn(NO_3)_2$ or HCl.

12. The method according to claim 9, further comprising copolymerizing the oligomer with a monomer to form a corrosion-resistant copolymer.

13. The method according to claim 9, wherein said composition is formed by curing an epoxy resin with said oligomer.

14. The method according to claim 13, further comprising heat curing the oligomer and epoxy resin at a temperature of at least 100° C.

15. The method according to claim 14 further comprising heat curing doping the oligomer with $Zn(NO_3)_2$ or HCl.

\* \* \* \* \*